United States Patent [19]

Ikezawa et al.

[11] 4,439,911
[45] Apr. 3, 1984

[54] METHOD OF MAKING AN OXYGEN SENSOR

[75] Inventors: Kenji Ikezawa, Yokohama; Hiroshi Takao, Kamakura; Satoshi Ambe, Yokosuka; Masaaki Uchida, Yokohama, all of Japan

[73] Assignee: Nissan Motor Co., Ltd., Yokohama, Japan

[21] Appl. No.: 442,231

[22] Filed: Nov. 16, 1982

Related U.S. Application Data

[62] Division of Ser. No. 220,153, Dec. 23, 1980, abandoned.

[30] Foreign Application Priority Data

Dec. 28, 1979 [JP] Japan .............................. 54-170445

[51] Int. Cl.³ ............................................. G01N 27/58
[52] U.S. Cl. ...................................... 29/570; 204/426
[58] Field of Search ....................... 204/425, 426, 1 S; 338/34; 422/94, 95, 96, 97; 73/23; 29/570

[56] References Cited

U.S. PATENT DOCUMENTS

| 4,040,930 | 9/1977 | Dillon ................................ 204/426 |
| 4,107,019 | 8/1978 | Takao et al. ....................... 204/425 |
| 4,123,344 | 10/1978 | Davis ................................. 204/428 |
| 4,193,965 | 3/1980 | Cullingford et al. ................ 422/95 |
| 4,206,173 | 6/1980 | Yamaguchi et al. ................. 422/98 |
| 4,207,159 | 6/1980 | Kimura et al. ..................... 204/425 |
| 4,224,113 | 9/1980 | Kimura et al. ..................... 204/1 T |
| 4,287,751 | 9/1981 | Yasuda et al. ......................... 73/23 |
| 4,303,613 | 12/1981 | Yasuda et al. ....................... 422/95 |

FOREIGN PATENT DOCUMENTS

| 2115619 | 10/1972 | Fed. Rep. of Germany ...... 204/428 |
| 2004067 | 3/1979 | United Kingdom ............... 204/426 |

*Primary Examiner*—G. L. Kaplan
*Attorney, Agent, or Firm*—Schwartz, Jeffery, Schwaab, Mack, Blumenthal & Koch

[57] ABSTRACT

At least a portion of an oxygen sensor element support to which portion an oxygen sensor element directly contacts is constructed of an heat insulating material having very low thermal conductivity, so that the heat release from the oxygen sensor element is minimized.

13 Claims, 14 Drawing Figures

FIG.4A
(PRIOR ART)
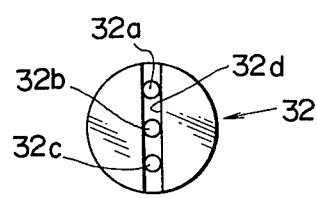
FIG.5
(PRIOR ART)
FIG.4B
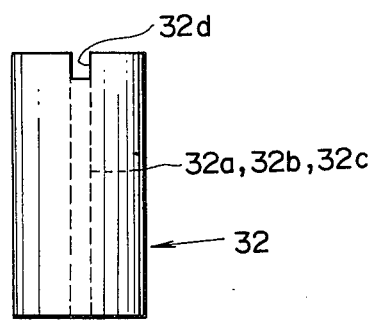
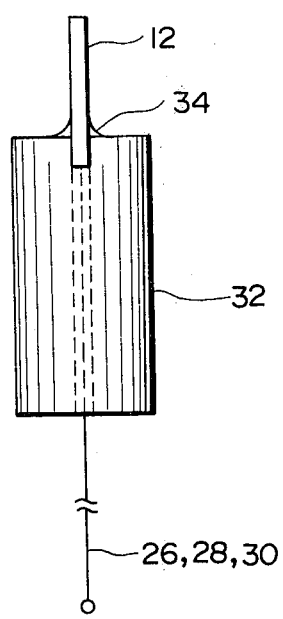
FIG.6
(PRIOR ART)
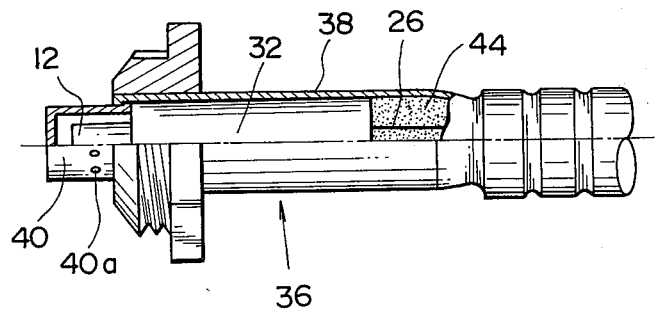

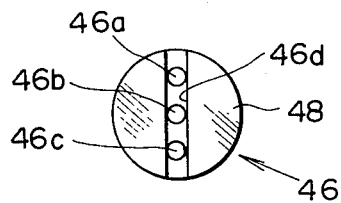
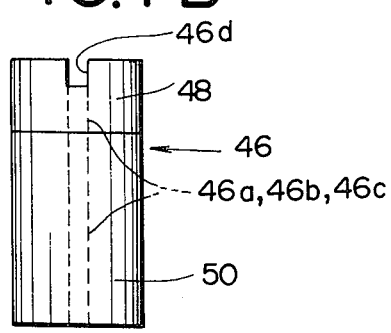
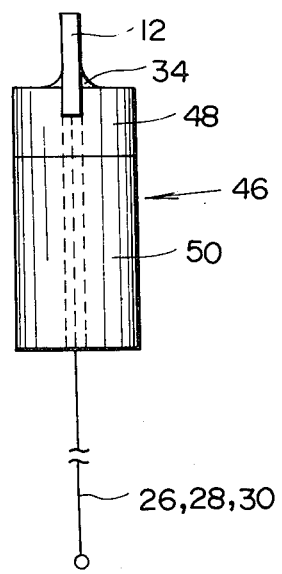
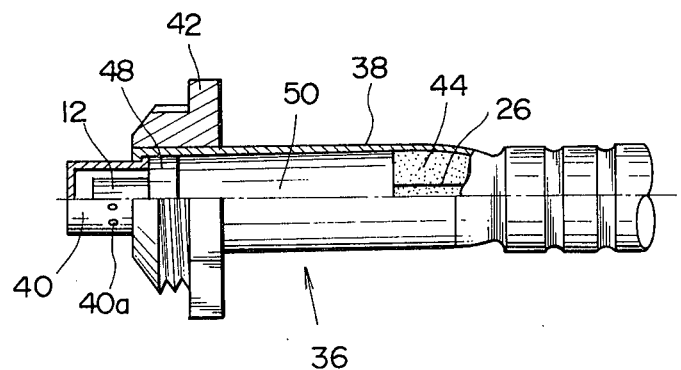

METHOD OF MAKING AN OXYGEN SENSOR

This is a division of application Ser. No. 220,153, filed Dec. 23, 1980 and now abandoned.

BACKGROUND OF THE INVENTION

1. Field of the Invention

The present invention relates in general to an oxygen sensor for measuring the oxygen concentration in a fluid, and more particularly to an oxygen sensor unit which comprises a so-called flat film type oxygen sensor element and an element support by which the sensor element is supported.

2. Description of the Prior Art

Flat film type oxygen sensor elements, which employ a flat solid electrolyte layer, show better performance with regard to EMF (electromotive force) characteristics and responsiveness as compared with tubular type oxygen sensors which employ a soloid electrolyte in the form of a tube. However, some oxygen sensor elements of the flat film type fail to exhibit their maximum possible performance because of use of an element support having poor thermal insulating characteristics. In fact, the usage of such element support causes considerable heat release from the sensor element at its base thereby preventing the sensor element from being kept at an effective operating temperature. This phenomenon becomes more critical when the sensor is exposed to a fluid having relatively low temperatures.

BRIEF SUMMARY OF THE INVENTION

According to the present invention, there is provided an oxygen sensor unit. The unit comprises an oxygen sensor element sensitive to oxygen in a fluid to produce a signal representative of the oxygen concentration in the fluid, and a support member supporting thereon the oxygen sensor element, wherein at least a portion of the support member to which portion the oxygen sensor element directly contacts is constructed of a heat insulating material which has a thermal conductivity lower than $0.01$ cal.cm/cm$^2$.sec.C.°.

It is an object of the present invention to provide an oxygen sensor unit comprising an oxygen sensor element and a support on which the element is supported, the support being constructed of a heat insulating material so that heat release from the sensor element is minimized.

BRIEF DESCRIPTION OF THE DRAWINGS

Other objects and advantages of the present invention will become clear from the following description when taken in conjunction with the accompanying drawings, in which:

FIGS. 4A and 4B are plan and front views of a conventionally used support for supporting the oxygen sensor element of FIG. 2;

FIG. 5 is a front view of an oxygen sensor unit consisting of the oxygen sensor element of FIG. 2 and the conventional support of FIGS. 4A and 4B;

FIG. 6 is a partially sectional view of an oxygen sensor holder having the oxygen sensor unit of FIG. 5 mounted therein;

FIGS. 7A and 7B are plan and front views of an improved support for supporting the oxygen sensor element of FIG. 2, the support being a part of the oxygen sensor unit according to the present invention;

FIG. 8 is a sectional view of the oxygen sensor unit according to the present invention, the sensor unit consisting of the oxygen sensor element of FIG. 2 and the improved support of FIGS. 7A and 7B;

FIG. 9 is a sectional view of an oxygen sensor holder having the assembled oxygen sensor unit of FIG. 8 of the invention mounted therein;

DETAILED DESCRIPTION OF THE INVENTION

Prior to describing the invention in detail, conventionally used oxygen sensor units will be outlined with reference to FIGS. 1 to 6 in order to clarify the invention.

Figure 1:
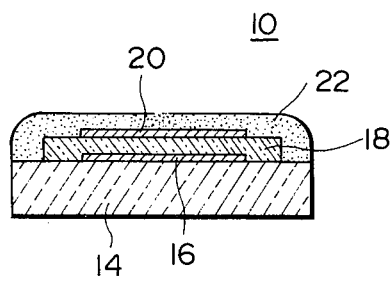
FIGS. 1 and 2 are schematically illustrated sectional views of flat film type oxygen sensor elements.
Figure 2:
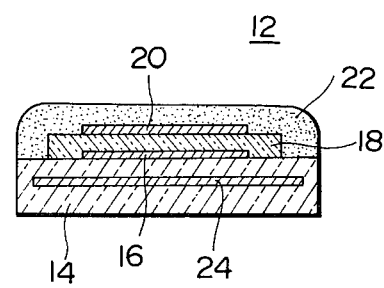

Referring to FIGS. 1 and 2, there are shown, in a sectional manner, conventional oxygen sensor elements of the flat film type. The oxygen sensor elements, which are designated by reference numerals 10 and 12 respectively, comprise a partition layer 14 of a ceramic designed to serve as a structural base member for the sensor element 10 or 12. In addition, there is a first or reference electrode layer 16 deposited on the partition layer 14, a layer 18 of an oxygen ion conductive solid electrolyte deposited on the first electrode layer 16, a second or measuring electrode layer 20 deposited on the solid electrolyte layer 18, and a protective layer 22 wholly and intimately covering both the second electrode layer 20 and the sides of the solid electrolyte layer 18. In the oxygen sensor element 12 of FIG. 2, an electric heater 24 is further provided which is embedded in the partition layer 14. As is known, the electric heater 24 is used for maintaining the oxygen sensor element 12 at a relatively high temperature.

Figure 3:
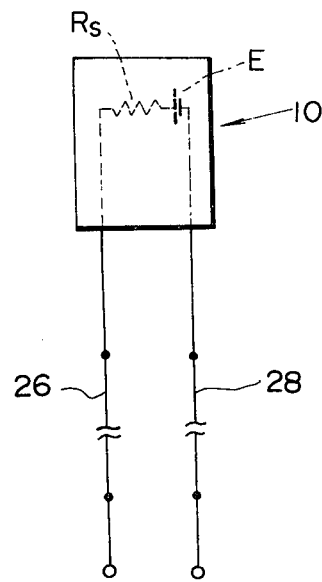
FIGS. 3 and 4 are illustrations for showing the electrical circuits arranged in the respective oxygen sensor elements of FIGS. 1 and 2.
Figure 4:
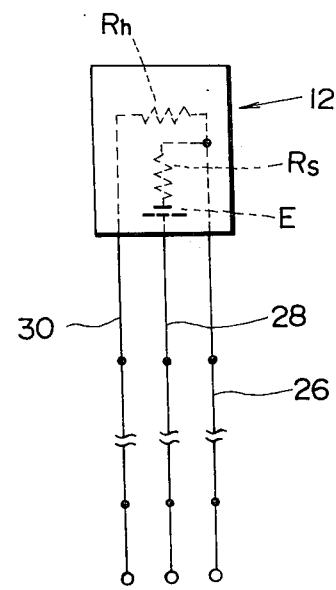

FIGS. 3 and 4 show electrical circuits or wirings applied to the oxygen sensor elements 10 and 12 respectively. In the circuits shown, $R_s$ represents an internal resistance of the solid electrolyte layer 18, E represents the electromotive force produced by the layer 18, and $R_h$ represents the electric resistance of the heater 24. The electromotive force is picked up by suitable lead wires 26 and 28 which are respectively connected to the first and second electrode layers 16 and 20 by suitable connecting technique, such as welding and brazing. In case of the oxygen sensor element 12, an additional lead wire 30 is employed which is connected to the electric heater 24 and to a suitable electric power source (not shown). As the material of the lead wires, platinum, nickel and copper may be employed.

When putting these oxygen sensor elements 10 and 12 into practical use, it is necessary to mount these elements 10 and 12 on a structurally dependable support because of the delicate and fragile construction of the elements 10 and 12.

A conventional support is shown in FIGS. 4A and 4B as being designated by numeral 32. The support 32 shown is designed to cooperate with the sensor element 12 of FIG. 2. The support 32 is constructed of alumina sinter and has a cylindrical form. As is understood from the drawings, three parallel longitudinally extending holes 32a, 32b and 32c are formed through the support 32 and a groove 32d is formed at one longitudinal end of the support 32 to be merged with the through holes 32a, 32b and 32c. As is shown in FIG. 5, upon assemblage, the lower section of the sensor element 12 is coupled in the groove 32d with the three wires 26, 28 and 30 passed through the holes 32a, 32b and 32c respectively, and an inorganic adhesive material 34 is applied to the portion where the sensor element 12 and the support 32 contact with each other, for assured connection therebetween.

FIG. 6 shows an oxygen sensor holder 36 having the assembled oxygen sensor unit (12+32) mounted therein, which is commonly used when measuring the oxygen concentration in an engine exhaust gas passing through an exhaust tube. The holder 36 comprises a cylindrical metallic sheath 38 within which the alumina sinter support 32 is tightly disposed, and a metallic louvered cap 40 mounted to an end of the sheath 38 to spacedly cover the sensor element 12 on the support 32. A coupling seat 42 having male screw threads thereon is securely mounted on the sheath 38 for removable connection with a tube through which a gas to be measured passes. The tail end of the sheath 38 is swaged as shown. Denoted by numeral 44 is an alumina powder sealant which is packed in the sheath 38. Upon connection of the holder 36 to the exhaust tube, the louvered cap 40 is exposed to the gas in the tube thereby enabling the gas to flow into and out of the cap through the openings 40a of the cap 40.

However, in using the above-mentioned holder 36 with the oxygen sensor unit (12+32) mounted therein, the following drawback is encountered, as a result of the poor thermal insulating characteristics possessed by the support 32 constructed of alumina sinter. When the oxygen sensor element 12 in the holder 36 is exposed to a fluid which is to be measured, there occurs a considerable heat transmittance from the oxygen sensor element 12 to the externally positioned metallic sheath 38 through the support 32 having poor thermal insulation characteristics. Thus, it has been difficult to rapidly warm up the oxygen sensor element 12 to a level at which it exhibits normal measuring operation, even when the heater 24 is energized to warm the element 12. In order to keep the temperature of the oxygen sensor element 12 at the normally operating level upon measuring a low temperature gas, a greater amount of electricity than that theoretically required in necessitated. A similar undesired drawback is encountered in another oxygen sensor unit which comprises the heaterless oxygen sensor element 10 and its associated support (not shown) constructed of alumina sinter.

The elimination of the above-mentioned drawback is an essential object of the present invention. An improved oxygen sensor unit according to the present invention will now be described.

Referring to FIGS. 7A and 7B, there is shown an improved support 46 which is a part of the oxygen sensor unit of the present invention. The support 46 shown is designed to cooperate with the oxygen sensor element 12 of FIG. 2. The support 46 comprises an upper cylindrical body 48 and a lower cylindrical body 50 which are coaxially connected as shown by FIG. 7B. The upper cylindrical body 48 is constructed of sintered mullite. When the body 48 is still in green condition, a groove 46d and three through holes 46a, 46b and 46c are formed therein. The lower cylindrical body 50 is constructed of sintered alumina. When the body 50 is still in green condition, three through holes 46a, 46b and 46c are formed therein. The green conditioned bodies 48 and 50 are fired at a temperature of about 1400° C. for about 3 hours to sinter these bodies. By occurrence of diffusion of atoms and/or ions during the sintering, the two bodies 48 and 50 are intimately and strongly bonded to each other. If desired, the connection of these bodies 48 and 50 may be made by the assistance of mullite slip or alumina slip applied to the contact faces of the bodies. With these procedures, there is produced the support 46 which includes two portions 48 and 50 having different thermal conductivities. As shown by FIG. 8, similar to the conventional sensor unit of FIG. 5, the oxygen sensor element 12 is grasped by the groove 46d of the upper body 48 with the three lead wires 26, 28 and 30 passed through the holes 46a, 46b and 46c respectively and an inorganic adhesive material 34 is applied to the portion where the sensor element 12 and the upper body 48 contact with each other, for assured connection therebetween.

As is shown by FIG. 9, the oxygen sensor unit (12+46) is mounted in the holder 36 in the same manner as in the case of the conventional oxygen sensor unit of FIG. 5.

Figure 10:
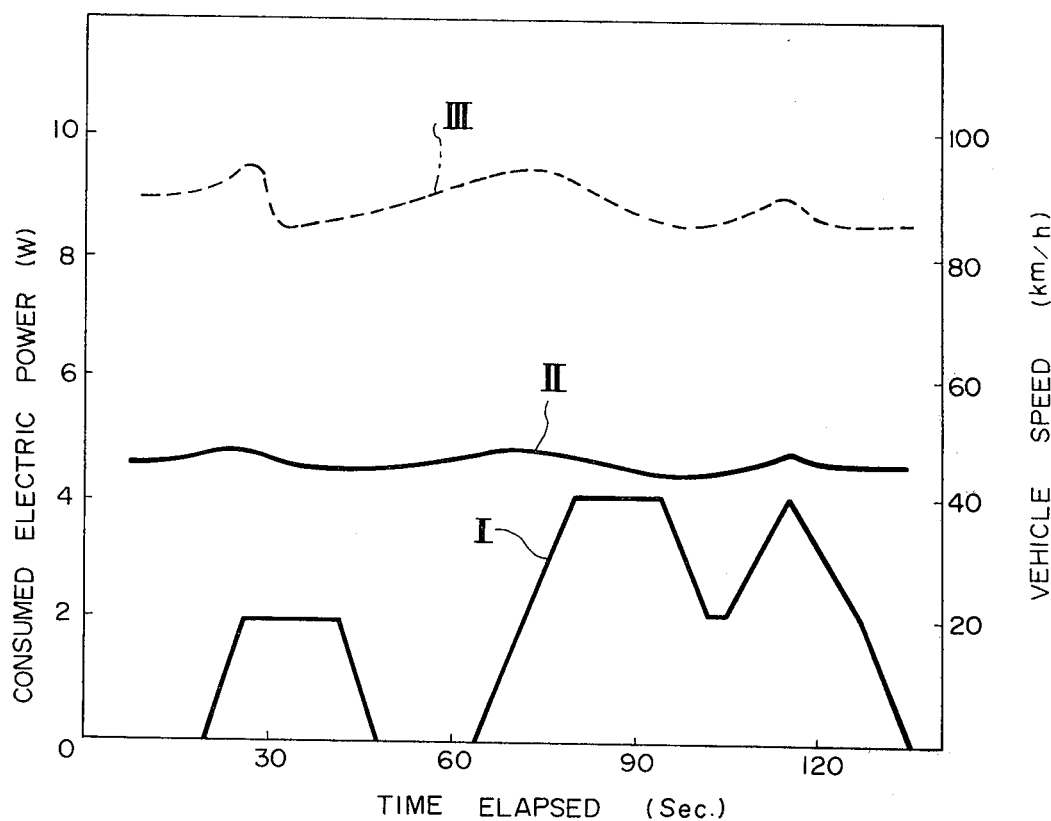
FIG. 10 is a graph showing results of an experiment, in which the relationship between a time elapsed and electric power consumed by a heater embedded in the oxygen sensor element is shown.

The oxygen sensor unit (12+46) of FIG. 8 was subjected to an automobile road test in which the electric power consumed by the heater 24 for maintaining the oxygen sensor element 12 at a given constant temperature was measured. For comparison, the conventional sensor unit (12+32) of FIG. 5 was subjected to the same test. The results of this test are shown by FIG. 10 in which line I (solid line) represents the vehicle speed, line II (solid line) represents the electric power consumed by the heater 12 cooperated with the sensor unit (12+46) of the present invention, and line III (broken line) represents the electric power consumed by the heater 12 cooperated with the conventional sensor unit (12+32) of FIG. 5. As will be understood from this graph, the electric consumption by the sensor unit according to the present invention is quite small as compared with the conventional sensor unit (12+32). This means that, in the oxygen sensor unit of the present invention, the heat generated by the heater 24 is effectively used for keeping the temperature of the sensor element 12 at the predetermined operational level. Use of the heat insulating member as the support of the sensor element 12 brings about the above-mentioned desired result.

Figure 11:
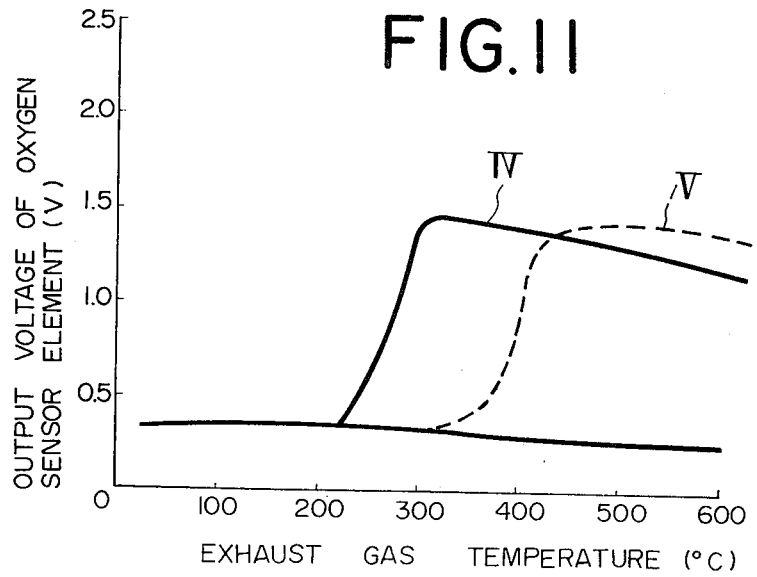
FIG. 11 is a graph showing results of another experiment, in which the relationship between the temperature of an exhaust gas to be measured and the output of the oxygen sensor element is shown.

As an alternative embodiment of the present invention, an oxygen sensor unit was provided which comprises the heaterless oxygen sensor element 10 of FIG. 1 and an element support which has substantially the same construction as the support 46 of FIGS. 7A and 8B. This alternative oxygen sensor unit was subjected to an automobile bench test in which the variation of the output power of the oxygen sensor element 10 relative to the variation of the exhaust gas temperature is measured. For comparison, a conventional oxygen sensor unit comprising the sensor element 10 of FIG. 1 and a support which has substantially the same construction as the conventional support 32 of FIGS. 4A and 4B was also subjected to the same test. The results of this test are shown by FIG. 11 in which line IV (solid line) represents the output voltage of the oxygen sensor element 10 of the unit of the invention, and line V (broken line) represents the output voltage of the sensor element 10 of the conventional sensor unit. As is understood from this graph, in the oxygen sensor unit of the present invention, the output voltage of the sensor element 10 is sufficiently gained even when the temperature of the exhaust gas to which the sensor element is exposed is relatively low in comparison with the conventional sensor unit. This means that, in the alternative embodiment of the present invention, the heat escaping of the sensor element 10 is quite low, as compared with the conventional one, by the use of the heat insulating member as the sensor support.

In general, the degree of heat transmittance per unit sectional area and unit time is represented by the following equation:

$$Q = \frac{k(T_s - T_e)}{d}$$

wherein:
k: thermal conductivity of the substance;
$T_s, T_e$: temperatures of two points on the substance;
d: distance between the two points of the substance With this equation, it will be appreciated that in order to minimize the heat transmittance, it is necessary to use, as a material of the oxygen sensor support, an insulating material having lower thermal conductivity.

As is known, in a substance being constructed of sintered material such as ceramics, the thermal conductivity "k" thereof is varied in accordance with the apparent specific gravity of the substance. In other words, as the apparent specific gravity is decreased, the thermal conductivity "k" lowers correspondingly.

In the the above-mentioned embodiments of the present invention, the oxygen sensor unit 46 consists of the upper cylindrical body 48 constructed of sintered mullite the thermal conductivity of which is lower than 0.01 cal.cm/cm²·sec.C.°, and the lower cylindrical body 50 constructed of sintered alumina the thermal conductivity of which is about 0.05 to 0.08 cal.cm/cm². It is also available to construct the entire of the support 46 with sintered mullite having lower thermal conductivity than 0.01 cal.cm/cm²·sec.C.°.

Experiments have revealed that in addition to the above-mentioned sintered mullite used as the material of the upper cylindrical body 48 of the support 46, it is also available to use other insulating sintered materials such as sintered forsterite, sintered steatite and sintered cordierite, which are shown in Table 1, each having a thermal conductivity lower than the value of 0.01 cal.cm/cm²·sec.C.°. Of course, the entire of the support 46 may be constructed of one of the listed materials. Experiments have further revealed that the desired results are also expected when at least a portion of the support 46 to which portion the oxygen sensor element 10 or 12 contacts is constructed of an insulating material having a thermal conductivity lower than the above-mentioned value. Experiments have further revealed that when the support 46 is constructed of very porous sintered material of alumina, the thermal conductivity of it becomes quite small, but it shows insufficient mechanical strength. Thus, this measure is not applied to an oxygen sensor unit which is mounted to an exhaust tube of an automotive engine. In selecting the material of the support 46, electrical insulation should be also taken into consideration because of dependable electrical insulation between adjacent lead wires which respectively pass through the holes of the support 46.

TABLE 1

| Material of the upper cylindrical body (48) of the support (46) | Water Absorption (%) | Flexural Rigidity (kg/cm²) | Thermal Conductivity (20° C.) (cal · cm/cm² · sec · C.°) | Insulation Resistance (MΩ) (500 C.°) |
|---|---|---|---|---|
| Cordierite (2MgO.2Al$_2$O$_3$.5SiO$_2$) | 1 | 1000 | 0.005 | 10 |
| Mullite (3Al$_2$O$_3$.2SiO$_2$) | 0 | 1400 | 0.005 | 10² |
| Steatite (MgO.SiO$_2$) | 0 | 1600 | 0.006 | 10² |
| Forsterite (2MgO.SiO$_2$) | 0 | 1500 | 0.008 | 10⁴ |

In production of the support 46 consisting of the upper and lower cylindrical bodies 48 and 50, selected one or two materials listed in the table-1 are prepared and mixed severally with organic binder or inorganic binder to form respective pasty compounds, and then these compounds are subjected to an extrusion process to provide green-conditioned articles shaped corresponding to the finished upper and lower cylindrical bodies 48 and 50 respectively. Then, these green-conditioned articles are fired to form sintered articles of the support 46. In particular, when producing the upper cylindrical body 48 with mullite, powdered mullite is mixed with CMC (carboxymethyl cellulose) as an organic binder, sodium pyrophosphate as a dispersing agent, and a very small amount of pulp waste fluid as a plasticizer and kneaded together to provide a pasty compound of them, and then the pasty compound is subjected to an extrusion moulding using a vacuum extrusion machine. The through holes 54a, 54b and 54c are formed at the time of processing the extrusion moulding. The moulded article thus formed is cut in predetermined lengths each and the pieces thus cut are subjected to a temporaty sintering process, forming the groove 46d. After this process, a substantially sintering process is carried out at a temperature of about 1400 C.° for 3 hours to obtain a finished article of the upper cylindrical body 48. The lower cylindrical body 50 of the support 46 is formed from any one of the materials listed in the table-1 by employing substantially the same production process as that mentioned in the case of the upper cylindrical body 48. As has been mentioned before, the upper and lower cylindrical bodies 48 and 50 are put on each other when they are still in the green condition, and then they are fired. Occurrence of diffusion of atoms or ions upon the sintering process brings about the secured connection between these two bodies 48 and 50.

Although, in the embodiments mentioned above, there are shown cases wherein the oxygen concentration sensing substance is constructed of the oxygen ion conductive solid electrolyte, such as CaO-ZrO$_2$ or $Y_2O_3$-$ZrO_2$, which generates electromotive force corresponding to the difference in oxygen partial pressure, it is available to use, as the oxygen concentration sensing substance, an oxide semiconductor, such as $TiO_2$ and $CoO$, the electric resistance of which changes in accordance with variation of the oxygen concentration in the atmosphere to be measured. In the latter case, the lead wires 26 and 28 may be adhesively bonded to respective electrode layers formed on the oxide semiconductor, or the lead wires may be embedded in the oxide semiconductor, for the electrical connection therebetween.

As is described in the above, in accordance with the present invention, at least a portion of a sensor element support 46 to which portion the oxygen sensor element 10 or 12 contacts directly is constructed of a heat insulating material having very low thermal conductivity (lower than 0.01 cal.cm/cm²·sec.C.°). Thus, in a case of the heaterless oxygen sensor element 10 of FIG. 1, the heat obtained from the outside is effectively used for keeping the element 10 at the predetermined desired temperature. Further in a case of the heater built-in type oxygen sensor element 12 of FIG. 12, the electric power consumed by the heater 24 is minimized.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method of maintaining a solid electrolytic oxygen sensor element of an oxygen sensor unit having a support member at an effective operating temperature, comprising:
   forming a first green conditioned body of a heat insulating material;
   forming a second green conditioned body of a ceramic material;
   forming a groove on a surface of said first body;
   aligning said first and second bodies to form said support members;
   sintering the aligned first and second bodies to intimately bond them together;
   mounting said solid electrolytic oxygen sensor element in said groove to form said oxygen sensor unit;
   wherein said heat insulating material has a lower thermal conductivity than said ceramic material, the thermal conductivity of said heat insulating material being less than on the order of about 0.01 cal.cm/cm²·sec.C.°.

2. The method of claim 1, further comprising the step of providing said sensor element with a heater.

3. The method of claim 1, wherein said heat insulating material is selected from the group consisting of sintered mullite, sintered cordierite, steatite, or fosterite.

4. The method of claim 3, including the step of mixing one or more materials of said group with a binder to form a pasty compound and extruding said pasty compound to form said first green cylindrical body.

5. The method of claim 4, wherein said compound further includes a dispersing agent and plasticizer.

6. The method of claim 4, wherein said step of extruding further comprises vacuum extrusion on molding said bodies in predetermined lengths, forming holes for said sensor element connections at the time of said extrusion molding, and wherein said groove portion for said sensor element is formed in said first body by temporary sintering.

7. The method of claim 1, wherein said first body comprises a lower cylinder and said second body comprises an upper cylinder and said step of aligning further includes axially aligning said upper and lower cylinders.

8. The method of claim 7, further comprising:
   providing parallel axial holes along said groove portion for passing connection means for said sensor element,
   providing cooperating axial holes in said lower cylinder in alignment with said axial holes along said groove portion whereby said connection means can be passed through said lower and upper cylinder portions for connection to said sensor element.

9. The method of claim 8, wherein said holes are formed when said upper and lower cylinders are in said green condition.

10. The method of claim 9, wherein said step of sintering further includes the step of firing said axially aligned cylinders at a temperature of about on the order of 1400° C. for about on the order of 3 hours.

11. The method of claim 8, further including the step of attaching said sensor element to said upper cylinder with an adhesive material whereby a sure connection is established.

12. The method of claim 7, wherein said upper and lower cylinders contact at contact faces and the step of axially aligning said upper and lower cylinders includes the step of applying a slip material to said contact faces.

13. The method of claim 12, wherein the slip material is in the form of the material of either said upper cylinder or said lower cylinder.

* * * * *